(12) United States Patent
Malic et al.

(10) Patent No.: US 11,753,485 B2
(45) Date of Patent: Sep. 12, 2023

(54) MICROFLUIDIC ASSISTED FABRICATION OF POLYMER MICROPARTICLE-METAL NANOPARTICLE COMPOSITES

(71) Applicant: NATIONAL RESEARCH COUNCIL OF CANADA, Ottawa (CA)

(72) Inventors: Lidija Malic, Saint Leonard (CA); Xuefeng Zhang, Boucherville (CA); Keith Morton, St-Bruno-de-Montarville (CA); Teodor Veres, Montreal (CA)

(73) Assignee: National Research Council of Canada, Ottawa (CA)

( * ) Notice: Subject to any disclaimer, the term of this patent is extended or adjusted under 35 U.S.C. 154(b) by 620 days.

(21) Appl. No.: 16/651,067

(22) PCT Filed: Sep. 25, 2018

(86) PCT No.: PCT/CA2018/051202
§ 371 (c)(1),
(2) Date: Mar. 26, 2020

(87) PCT Pub. No.: WO2019/060989
PCT Pub. Date: Apr. 4, 2019

(65) Prior Publication Data
US 2020/0223948 A1 Jul. 16, 2020

Related U.S. Application Data

(60) Provisional application No. 62/563,206, filed on Sep. 26, 2017.

(51) Int. Cl.
*C08F 2/01* (2006.01)
*C08F 222/10* (2006.01)
(Continued)

(52) U.S. Cl.
CPC .............. *C08F 2/01* (2013.01); *C08F 2/44* (2013.01); *C08F 2/48* (2013.01); *C08F 222/102* (2020.02);
(Continued)

(58) Field of Classification Search
CPC ......................................... C08F 2/01
See application file for complete search history.

(56) References Cited

U.S. PATENT DOCUMENTS

2006/0257485 A1* 11/2006 Kumacheva ......... C08G 83/001
424/490
2011/0183140 A1 7/2011 Fourkas et al.

FOREIGN PATENT DOCUMENTS

EP        3073321 A1    9/2016
JP      2007089446 A    4/2007
(Continued)

OTHER PUBLICATIONS

European Search Report—EP 18860753.5 dated Apr. 29, 2021.
(Continued)

*Primary Examiner* — William D Young
(74) *Attorney, Agent, or Firm* — Bereskin & Parr LLP/S.E.N.C.R.L., s.r.l.; Michael Fenwick

(57) ABSTRACT

The present application relates to polymer microparticle-metal nanoparticle composites, to methods of preparing polymer microparticle-metal nanoparticle composites and to uses of such composites. The methods comprise introducing into a microfluidic device, a composition comprising: a cationic metal nanoparticle precursor; a polymer microparticle precursor that comprises a plurality of photopolymerizable groups; and a photoreducer-photoinitiator; then irradiating the composition under conditions to simultaneously reduce the cationic metal and polymerize the photopolymerizable groups to obtain the composite.

17 Claims, 13 Drawing Sheets

(51) Int. Cl.
- C08F 2/44 (2006.01)
- C08F 2/48 (2006.01)
- C08K 3/08 (2006.01)
- C08K 5/053 (2006.01)
- C12Q 1/686 (2018.01)
- B82Y 30/00 (2011.01)
- B82Y 40/00 (2011.01)

(52) U.S. Cl.
CPC ............... *C08K 3/08* (2013.01); *C08K 5/053* (2013.01); *C12Q 1/686* (2013.01); *B82Y 30/00* (2013.01); *B82Y 40/00* (2013.01); C08K 2003/0831 (2013.01); C08K 2201/011 (2013.01)

(56) References Cited

FOREIGN PATENT DOCUMENTS

| | | |
|---|---|---|
| JP | 20121219133 A | 7/2012 |
| JP | 2013509585 A | 3/2013 |
| JP | 2013512291 A | 4/2013 |
| JP | 2015511124 A | 4/2015 |
| WO | WO2004081072 | 9/2004 |
| WO | WO2016/046847 | 3/2016 |

OTHER PUBLICATIONS

Abalde-Cela, Sara, et al. "Loading of exponentially grown LBL films with silver nanoparticles and their application to generalized SERS detection." Angewandte Chemie 121.29 (2009): 5430-5433.

Baah, David et al. Microfluidic Synthesis and Post Processing of Non-Spherical Polymeric Microparticles. Microfluid Nanofluid. 12:657-662, 2012.

Dendukuri, D. et al., "Continuous-flow lithography for high-throughput microparticle synthesis" Nat. Mater. 2006, 5, 365-369.

Eustis, Susie, and Mostafa A. El-Sayed. "Why gold nanoparticles are more precious than pretty gold: noble metal surface plasmon resonance and its enhancement of the radiative and nonradiative properties of nanocrystals of different shapes." Chemical Society Reviews 35.3 (2006): 209-217.

Farah, Abdiaziz A., Ramon A. Alvarez-Puebla, and Hicham Fenniri. "Chemically stable silver nanoparticle-crosslinked polymer microspheres." Journal of Colloid and Interface Science 319.2 (2008): 572-576.

Gunther, P.M., et al.,"Introduction of surface-modified Au-nanoparticles into the microflow-through polymerization of styrene"— Chemical Engineering Journal, Jan. 16, 2008 (Jan. 16, 2008), p. S126.

Kohler, J. M., et al.—"Continuous-flow preparation of nanoporous metal/polymer composite particles by in situ synthesis of silver nanoparticles in photopolymerized acrylate/diethylene glycol droplets", J Mater. Sci., 2013, 48, p. 2158-2166.

Kraus, I. et al.—"Continuous-Microflow Synthesis and Morphological Characterization of Multiscale Composite Materials Based on Polymer Microparticles and Inorganic Nanoparticles"—J. Flow Chem. , 2014, 4(2), p. 72-78.

Li, Huilin et al. Optical Sensing Properties of Au Nanoparticle/Hydrogel Composite Microbeads Using Droplet Microfluidics. Nanotechnology. 28:1-8, 2017.

Nikunkjkumar Visaveliya, et al.—"Microfluidic Assisted Synthesis of Multipurpose Polymer Nanoassembly Particles for Fluorescence, LSPR, and SERS Activities", Small, 2015, 11(48), p. 6435-6443.

Shum, Ho Cheung, et al. "Droplet Microfluidics for Fabrication of Non-Spherical Particles." Macromolecular rapid communications 31.2 (2010): 108-118.

I Solvas, Xavier Casadevall. "Droplet microfluidics: recent developments and future applications." Chemical Communications 47.7 (2011): 1936-1942.

Teh, Shia-Yen, et al. "Droplet microfluidics." Lab on a Chip 8.2 (2008): 198-220.

Trojanowska, Anna, et al. "Plasmonic-polymer hybrid hollow microbeads for surface-enhanced Raman scattering (SERS) ultradetection." Journal of Colloid and Interface Science 460 (2015): 128-134.

Von Werne, Timothy, and Timothy E. Patten. "Preparation of structurally well-defined polymer-nanoparticle hybrids with controlled/living radical polymerizations." Journal of the American Chemical Society 121.32 (1999): 7409-7410.

Wilhelm, T. S. "Microdroplet fabrication of silver-agarose nanocomposite beads for SERS optical accumulation." Soft Matter 7.4 (2011): 1321-1325.

Xu, Shengqing, et al. "Generation of monodisperse particles by using microfluidics: control over size, shape, and composition." Angewandte Chemie117.5 (2005): 734-738.

Yagci, Yusuf, Marco Sangermano, and Giancarlo Rizza. "In situ synthesis of gold-cross-linked poly (ethylene glycol) nanocomposites by photoinduced electron transfer and free radical polymerization processes." Chemical Communications 24 (2008): 2771-2773.

Japanese First Office Action dated Oct. 7, 2022.

\* cited by examiner

MICROFLUIDIC ASSISTED FABRICATION OF POLYMER MICROPARTICLE-METAL NANOPARTICLE COMPOSITES

CROSS-REFERENCE TO RELATED APPLICATIONS

The present application is a national phase entry of PCT/CA2018/051202 filed Sep. 25, 2018, which claims the benefit of priority from co-pending U.S. provisional application No. 62/563,206 filed on Sep. 26, 2017, the contents of which are incorporated herein by reference in their entirety.

FIELD

The present application relates to polymer microparticle-metal nanoparticle composites, to methods of preparing polymer microparticle-metal nanoparticle composites and to uses of such composites.

BACKGROUND

Metallic nanoparticles exhibit advantageous geometry and size-related properties that differ significantly from those observed in the corresponding bulk materials. For instance, plasmonic nanoparticles, unlike normal surface plasmons, exhibit unique scattering, absorbance and light coupling properties based on their geometries and relative positions[1]. Such properties have made them the focus of research in numerous applications, including but not limited to spectroscopy, enhanced imaging, drug delivery, cancer treatment and solar cells. However, current methods for fabrication of active plasmonic materials either suffer from intrinsic inhomogeneities (batch methods) or require highly specialized and expensive equipment (physical evaporation with ion or electron beam lithography) thus limiting their application[2].

To address the above issues, colloidal fabrication of plasmonic substrates, by combining metallic nanoparticles with non-plasmonic materials acting as a support or a matrix, has emerged as one of the promising fabrication methods due to several potential advantages. The advantages of these composite microparticles may, for example, include the formation of stable plasmonic signals, increase in size from nm to μm scale for easier integration into sensing devices and/or the development of better analyte trapping capability[3].

Yagci et al. reported UV induced radical polymerization of an acrylic resin (poly(ethylene glycol diacrylate, PEGDA) and gold nanoparticle formation by the reduction of gold (III) chloride hydrate ($HAuCl_4$) in the presence of a photoinitiator (Irgacure 2959)[4].

Different materials and fabrication methods have been used to produce composite colloids, including suspension polymerization[3], radical living polymerization[5] and microfluidic flow focusing[6]. These fabrication methods rely on the mixing of the liquid phases where the solubility of the polymer is much greater than that of the nanoparticles, thus resulting in a low amount of trapped metallic nanoparticles which may, for example, limit the generation of "hot spots" and signal enhancement capability of the colloids.

To increase the nanoparticle content beyond 1%, layer-by-layer protocols have been employed[7], however these techniques are generally time-consuming and unsuitable for the batch fabrication of discrete microparticles.

Phase-inversion precipitation methods could also potentially be used in order to reduce the amount of polymer and thus increase the nanoparticle content[2,8]. Phase-inversion precipitation methods can allow metal content of up to 10% in the colloid. However, this method also requires pre-mixing of nanoparticles with the matrix which increases the complexity of the fabrication (i.e. requires pre-synthesis of metallic nanoparticles). Additionally, control of nanoparticle dispersion within the matrix may be complex and challenging, limiting its interest for practical applications. Finally, this batch technique results in polydisperse microparticles which may not be suitable for industrial applications due to issues of repeatability and/or robustness.

In microfluidics, fluids may be manipulated and controlled, typically in the range of microliters ($10^{-6}$ L) to picoliters ($10^{-12}$ L), in networks of channels with dimensions which may range from tens to hundreds of micrometers. Continuous-flow microfluidics technologies are based on the manipulation of continuous liquid flow through microfabricated channels. In contrast, droplet-based microfluidics technologies use discrete volumes of fluids in immiscible phases with low Reynolds number and laminar flow regimes. The two immiscible phases used in droplet-based microfluidics are typically referred to as the continuous phase (the medium wherein the droplets are generated) and the dispersed phase (the droplet phase). Droplet microfluidics allows generation of uniform Droplets® and may be used, for example, to prepare highly monodisperse particles[10].

SUMMARY

Polymer microparticle-metal nanoparticle composites were prepared via irradiating microdroplets comprising the respective precursors in the presence of a photoreducer-photoinitiator. The polymer microparticle precursors were poly(ethylene glycol)-diacrylate (PEGDA) and ethoxylated trimethylolpropane triacrylate (ETPTA) which, in some experiments, were reacted with the bifunctional cross-linker dithiothreitol (DTT) prior to irradiation. The metal nanoparticle precursor was $HAuCl_4$ in which the $Au^{3+}$, under the irradiation conditions used, was reduced to $Au^0$. A uniform distribution of gold nanoparticles within the polymeric microparticles was observed when the bi-functional cross-linker was used, while gold nanoparticle concentration in the center of the fabricated microparticles occurred when the bi-functional cross-linker was not used.

Accordingly, the present application includes a method for preparing a polymer microparticle-metal nanoparticle composite, the method comprising:
  introducing into a microfluidic device, a composition comprising:
    a cationic metal nanoparticle precursor;
    a polymer microparticle precursor that comprises a plurality of photopolymerizable groups; and
    a photoreducer-photoinitiator; and
  irradiating the composition under conditions to simultaneously reduce the cationic metal and polymerize the photopolymerizable groups to obtain the polymer microparticle-metal nanoparticle composite.

The present application also includes a polymer microparticle-metal nanoparticle composite as well as a surface-functionalized polymer microparticle-metal nanoparticle composite. The present application also includes a polymer microparticle-metal nanoparticle composite comprising a uniform distribution of metal nanoparticles embedded in a polymeric resin microparticle, the polymeric resin comprising a plurality of metal-anchoring groups, the metal anchoring groups anchored to the nanoparticles. In some embodiments, the composites of the present application are prepared by a method for preparing polymer microparticle-metal nanoparticle composites of the present application.

The present application also includes a drug delivery system comprising a polymer microparticle-metal nanoparticle composite of the application.

The present application also includes uses of the polymer microparticle-metal nanoparticle composites of the application. In some embodiments, the uses of the composites are in drug delivery, colorimetric sensors, plasmonic bead heaters, and as a site for polymerase chain reaction (PCR).

Other features and advantages of the present application will become apparent from the following detailed description. It should be understood, however, that the detailed description and the specific examples while indicating embodiments of the application are given by way of illustration only, since various changes and modifications within the spirit and scope of the application will become apparent to those skilled in the art from this detailed description.

BRIEF DESCRIPTION OF THE DRAWINGS

The present application will now be described in greater detail with reference to the drawings in which.

DETAILED DESCRIPTION

I. Definitions

Figure 1:
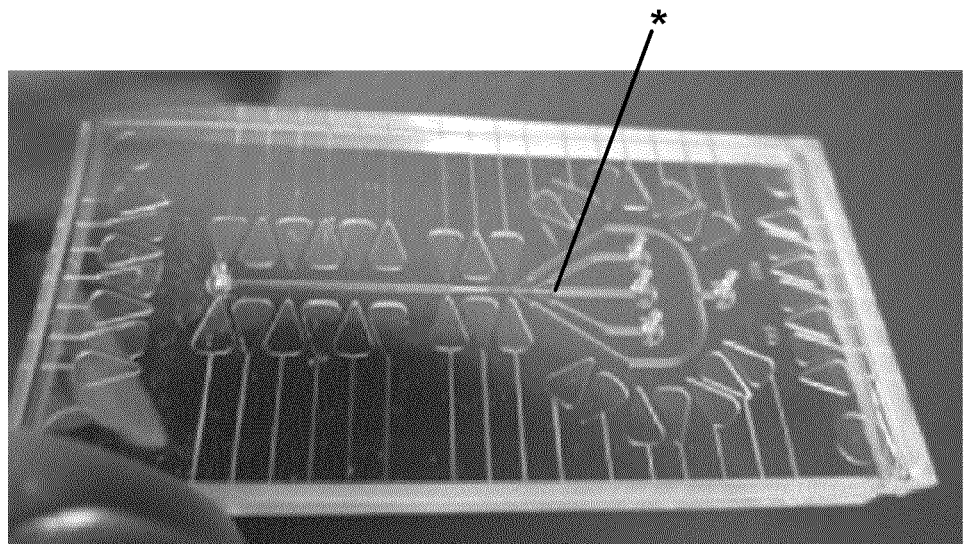
FIG. 1 is a photograph of a droplet microfluidics flow-focusing (microemulsion) device according to an embodiment of the present application.

Unless otherwise indicated, the definitions and embodiments described in this and other sections are intended to be applicable to all embodiments and aspects of the present application herein described for which they are suitable as would be understood by a person skilled in the art.

In understanding the scope of the present application, the term "comprising" and its derivatives, as used herein, are intended to be open ended terms that specify the presence of the stated features, elements, components, groups, integers, and/or steps, but do not exclude the presence of other unstated features, elements, components, groups, integers and/or steps. The foregoing also applies to words having similar meanings such as the terms, "including", "having" and their derivatives. The term "consisting" and its derivatives, as used herein, are intended to be closed terms that specify the presence of the stated features, elements, components, groups, integers, and/or steps, but exclude the presence of other unstated features, elements, components, groups, integers and/or steps. The term "consisting essentially of", as used herein, is intended to specify the presence of the stated features, elements, components, groups, integers, and/or steps as well as those that do not materially affect the basic and novel characteristic(s) of features, elements, components, groups, integers, and/or steps.

Terms of degree such as "substantially", "about" and "approximately" as used herein mean a reasonable amount of deviation of the modified term such that the end result is not significantly changed. These terms of degree should be construed as including a deviation of at least ±5% of the modified term if this deviation would not negate the meaning of the word it modifies.

The term "and/or" as used herein means that the listed items are present, or used, individually or in combination. In effect, this term means that "at least one of" or "one or more" of the listed items is used or present.

As used in this application, the singular forms "a", "an" and "the" include plural references unless the content clearly dictates otherwise. For example, an embodiment including "a polymer microparticle precursor" should be understood to present certain aspects with one polymer microparticle precursor or two or more additional polymer microparticle precursors. In embodiments comprising an "additional" or "second" component, such as an additional or second polymer microparticle precursor, the second component as used herein is chemically different from the other components or first component. A "third" component is different from the other, first, and second components, and further enumerated or "additional" components are similarly different.

In embodiments of the present application, the compounds described herein have at least one asymmetric center. Where compounds possess more than one asymmetric center, they may exist as diastereomers. It is to be further understood that while the stereochemistry of the compounds may be as shown in any given compound listed herein, such compounds may also contain certain amounts (e.g. less than 20%, optionally less than 10%, optionally less than 5%, optionally less than 1%) of compounds having alternate stereochemistry.

The term "suitable" as used herein means that the selection of specific reagents or conditions will depend on the reaction being performed and the desired results, but none-the-less, can generally be made by a person skilled in the art once all relevant information is known.

The term "dithiothreitol" and the abbreviation "DTT" refer to a compound having the following structure:

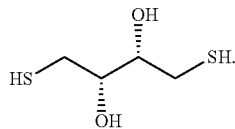

The term "poly(ethylene glycol)-diacrylate" and the abbreviation "PEGDA" as used herein refer to a monomer having the following structure:

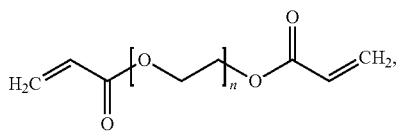

wherein n is dependent on the molecular weight of the PEGDA. For example, commercial sources of PEGDA include those available from Aldrich having an average $M_n$ of about 200, 575 and 700.

The term "ethoxylated trimethylolpropane triacrylate" and the abbreviation "ETPTA" as used herein refer to a monomer having the following structure:

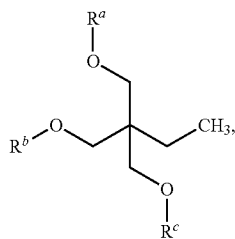

wherein $R^a$, $R^b$ and $R^c$ have the structure:

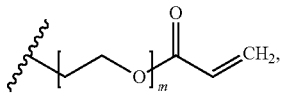

wherein each m may be the same or different and is dependent on the molecular weight of the ETPTA. For example, commercial sources of ETPTA include those available from Aldrich having an average $M_n$ of about 428, 692 and 912 as well as those available from Sartomer having a molecular weight of 428 g/mol (SR-454), 693 g/mol (SR-502) and 956 g/mol (SR-9035).

The term "metal-anchoring group" as used herein refers to a functional group capable of bonding to a surface of a metal nanoparticle.

The term "cationic metal nanoparticle precursor" as used herein refers to a compound in which the metal exists in cationic form and is reduced under the conditions used for photopolymerization in the methods for preparing a polymer microparticle-metal nanoparticle composite of the present application.

The term "DNA probe" as used herein refers to a single-stranded DNA molecule that is capable of detecting the presence of a target complementary nucleic acid sequence via hybridization.

The term "antibody" as used herein includes any antibody that binds to a desired antigen. In some embodiments, the antibody is a monoclonal antibody, polyclonal antibody, multispecific antibody or bispecific antibody.

The term "aptamer" as used herein refers to an oligonucleotide or peptide molecule that is capable of binding to a specific target molecule. In some embodiments, the aptamer is obtained by selecting the desired aptamer from a random sequence pool. In some embodiments, the aptamer is a single-stranded DNA or RNA oligonucleotide. In some embodiments, the aptamer is a peptide aptamer. Peptide aptamers consist essentially of one or more peptide loops of variable sequence coupled to a protein scaffold.

The term "primer" as used herein in reference to PCR means a short strand of DNA (for example, about 18-22 bases) that is capable of serving as a starting point for DNA synthesis in a PCR method.

The term "subject" as used herein includes all members of the animal kingdom including mammals, and suitably refers to humans.

The term "pharmaceutically acceptable" means compatible with the treatment of subjects such as humans.

The term "administered" as used herein means administration of an effective amount of a drug or a metal nanoparticle to a cell.

As used herein, the terms "effective amount" or "therapeutically effective amount" and the like mean an amount effective, at dosages and for periods of time necessary to achieve a desired result. For example, in the context of treating cancer, an effective amount of an anti-cancer drug or gold nanoparticle is an amount that, for example, reduces the cancer compared to the cancer without administration of the anti-cancer drug or gold nanoparticle. Effective amounts may vary according to factors such as the disease state, age, sex, weight and/or species of the subject. The amount of a given drug or gold nanoparticles that will correspond to such an amount will vary depending upon various factors, such as the given drug, the pharmaceutical formulation, the route of administration, the type of condition, disease or disorder being treated, the identity of the subject being treated, and the like, but can nevertheless be routinely determined by one skilled in the art.

The terms "to treat", "treating" and "treatment" as used herein and as is well understood in the art, means an approach for obtaining beneficial or desired results, including clinical results. Beneficial or desired clinical results include, but are not limited to, alleviation or amelioration of one or more symptoms of a disease, disorder or condition, diminishment of extent of a disease, disorder or condition, stabilized (i.e. not worsening) state of a disease, disorder or condition, preventing spread of a disease, disorder or condition, delay or slowing of the progression of a disease, disorder or condition, amelioration or palliation of the state of a disease, disorder or condition, diminishment of the reoccurrence of a disease, disorder or condition, and remission of a disease, disorder or condition (whether partial or total), whether detectable or undetectable. "To treat", "treating" and "treatment" can also mean prolonging survival as compared to expected survival if not receiving treatment. "Treating" and "treatment" as used herein also include prophylactic treatment. For example, a subject with early cancer can be treated to prevent progression, or alternatively a subject in remission can be treated to prevent recurrence.

II. Methods of Preparation

Polymer microparticle-metal nanoparticle composites were prepared via irradiating microdroplets comprising the respective precursors in the presence of a photoreducer-photoinitiator. The polymer microparticle precursors were poly(ethylene glycol)-diacrylate (PEGDA) and ethoxylated trimethylolpropane triacrylate (ETPTA) which, in some experiments, were reacted with the bifunctional cross-linker dithiothreitol (DTT) prior to irradiation. The metal nanoparticle precursor was $HAuCl_4$ in which the $Au^{3+}$, under the irradiation conditions used, was reduced to $Au^0$. A uniform distribution of gold nanoparticles within the polymeric microparticles was observed when the bi-functional cross-linker was used, while gold nanoparticle concentration in the center of the fabricated microparticles occurred when the bi-functional cross-linker was not used.

Accordingly, the present application includes a method for preparing a polymer microparticle-metal nanoparticle composite, the method comprising:
  introducing into a microfluidic device, a composition comprising:
    a cationic metal nanoparticle precursor;
    a polymer microparticle precursor that comprises a plurality of photopolymerizable groups; and
    a photoreducer-photoinitiator; and
  irradiating the composition under conditions to simultaneously reduce the cationic metal and polymerize the photopolymerizable groups to obtain the polymer microparticle-metal nanoparticle composite.

In some embodiments, the composition further comprises an agent that caps and/or stabilizes the nanoparticles. The term "caps" as used herein in reference to an agent that caps nanoparticles refers to an agent that may inhibit and/or prevent the nanoparticles from growth. The term "stabilizes" as used herein in reference to an agent that stabilizes nanoparticles refers to an agent that may inhibit and/or prevent the nanoparticles from agglomeration. In an embodiment, the agent that caps and/or stabilizes the nanoparticles is a polymer or a surfactant. Suitable polymers and surfactants for capping and/or stabilizing nanoparticles are known and can be selected by a person skilled in the art. In an embodiment, the agent that caps and/or stabilizes the nanoparticles is polyethyleneimine or polyvinyl alcohol. In another embodiment of the present application, the agent that caps and/or stabilizes the nanoparticles surfactant is oleylamine.

In the studies described hereinbelow, a uniform gold nanoparticle distribution within the polymer microparticles was observed when the polymer microparticle precursor was prepared by a method comprising reacting the monomer poly(ethylene glycol)-diacrylate (PEGDA) with the metal-anchoring group dithiothreitol (DTT) to obtain the corresponding polymer microparticle precursor. A uniform metal nanoparticle distribution may also be obtained when the polymer microparticle precursor comprises other metal-anchoring groups.

Accordingly, in some embodiments, the polymer microparticle precursor further comprises a plurality of metal-anchoring groups. The metal-anchoring groups can be any suitable metal-anchoring groups. In an embodiment, the metal anchoring groups are thiols, primary amines, silanes or combinations thereof. In another embodiment, the metal anchoring groups are thiols.

In some embodiments, the conditions comprise forming droplets of the composition then irradiating the droplets. Suitable conditions and devices for droplet-based microfluidics are known and can be selected by the person skilled in the art. In an embodiment, the microfluidics device comprises a T-junction geometry, a co-flow geometry or a flow-focusing geometry for forming the droplets. In an embodiment, the microfluidics device comprises a flow-focusing junction and droplets are formed by flowing the composition as a dispersed phase and an oil solution as a continuous phase to obtain an emulsion comprising droplets of the composition in the oil solution. In an embodiment, the method comprises irradiating the droplets with a point source of the radiation as they flow from the flow-focusing junction. In an alternative embodiment, the method comprises collecting the droplets and exposing the collected droplets in batch format using the source of the radiation. The oil phase is any suitable oil phase that is immiscible with the dispersed phase. In an embodiment, the oil phase comprises a hydrocarbon oil or mixtures thereof, a fluorinated oil or mixtures thereof and/or a silicone oil or mixtures thereof. In another embodiment, the droplets have an average diameter of from about 1 μm to about 1,000 μm. In a further embodiment, the droplets have an average diameter of from about 1 μm to about 100 μm.

In some embodiments, the conditions comprise flowing the composition through a microchannel in the microfluidic device and irradiating the flowing composition through a mask defining a microparticle shape. Suitable conditions and devices for continuous-flow microfluidics and irradiating a composition flowing through a microchannel in such devices through a mask are known and can be selected by a person skilled in the art. In an embodiment, the conditions comprise a projection photolithography technique[11] comprising using the objective of an optical microscope to irradiate the composition flowing through the microchannel through the mask. It will be appreciated by a person skilled in the art that the yield of such conditions may, for example, be lower than conditions comprising forming droplets of the composition. However, by using the conditions comprising irradiating through a mask, the microparticle shape is not limited to spheroids; it may, for example, be of any shape which is defined by the mask. In an embodiment, the shape is designed using CAD software. Suitable software for drafting such shapes can be selected by a person skilled in the art.

The microfluidic device is any suitable microfluidics device, the selection of which can be made by a person skilled in the art. In an embodiment, the microfluidics device is fabricated from silicon, glass, polydimethylsiloxane (PDMS), a thermoplastic polymer (such as but not limited to cyclic olefin copolymer (COC), poly(methyl methacrylate) (PMMA), polycarbonate (PC), polystyrene (PS)) or a thermoplastic elastomer using photolithography, wet or dry etching, soft-lithography, hot-embossing, nanoimprinting or injection-molding. In an embodiment, the microfluidics device is fabricated by a method comprising photolithography to fabricate a mold; hot embossing using the mold to pattern channels in a suitable thermoplastic polymer (e.g. COC); and enclosing the thermoplastic polymer with patterned channels in a suitable thermoplastic elastomer (e.g. a suitable Mediprene™ compound available from HEXPOL TPE).

The cationic metal nanoparticle precursor can be any suitable cationic metal nanoparticle precursor. In an embodiment, the cationic metal nanoparticle precursor is a cationic gold nanoparticle precursor, a cationic silver nanoparticle precursor, a cationic copper nanoparticle precursor or combinations thereof. In a further embodiment, the cationic metal nanoparticle precursor is a cationic gold nanoparticle precursor. In another embodiment, the cationic gold nanoparticle precursor is a gold chloride. In another embodiment, the cationic metal nanoparticle precursor is a cationic silver nanoparticle precursor. In a further embodiment, the cationic silver nanoparticle precursor is silver nitrate. In another embodiment, the cationic metal nanoparticle precursor is a cationic copper nanoparticle precursor. In a further embodiment, the cationic copper nanoparticle precursor is copper sulfate. In another embodiment, the cationic metal nanoparticle precursor is a gold chloride, silver nitrate, copper sulfate or combinations thereof. In another embodiment, the gold chloride is $HAuCl_4$.

In an embodiment, the cationic metal nanoparticle precursor is present in an amount of from about 0.1% wt to about 30% wt, based on the total weight of the composition. The color of the microparticles can be varied, for example, based on the concentration of the cationic metal nanoparticle precursor. In some embodiments, the color of the microparticle ranges from pale pink to dark purple when the cationic metal nanoparticle precursor is present in an amount of from about 0.1% wt to about 10% wt. In another embodiment, the method is for preparing a plasmonic heater and a high concentration (e.g. greater or equal to about 100 mg/mL) of the cationic metal nanoparticle precursor is used. In another embodiment, the cationic metal nanoparticle precursor is present in a concentration of from about 50 mg/mL to about 150 mg/mL or about 100 mg/mL.

The photopolymerizable groups can be any suitable photopolymerizable groups. In an embodiment, the photopolymerizable groups are selected from acrylate groups, epoxy groups, cyclic siloxane groups or a combination thereof. The cyclic siloxane group is any suitable cyclic siloxane group that undergoes ring-opening polymerization under the conditions used for photopolymerization in the methods for preparing a polymer microparticle-metal nanoparticle composite of the present application. In another embodiment, the cyclic siloxane groups have a ring size of 6, 8 or 10. In a further embodiment, the cyclic siloxane group is a cyclic dimethylsiloxane group. In another embodiment, the photopolymerizable groups are acrylate groups.

In an embodiment, the polymer microparticle precursor is obtained from a method comprising:

reacting a monomer comprising two or more photopolymerizable groups with an anchor precursor comprising at least one metal-anchoring group and at least one group that will react with the photopolymerizable group.

In an embodiment, an aqueous solution of the monomer is reacted with an aqueous solution of the anchor precursor.

In an embodiment, the at least one metal-anchoring group and the at least one group that will react with the photopolymerizable group are the same and the anchor precursor is a bi-functional thiol, bi-functional primary amine or bi-functional silane. In an embodiment, the anchor precursor is dithiothreitol.

In an embodiment, the monomer further comprises an oligomeric poly(ethylene glycol). In another embodiment, the monomer is poly(ethylene glycol)-diacrylate (PEGDA) or ethoxylated trimethylolpropane triacrylate (ETPTA). In a further embodiment, the monomer is poly(ethylene glycol)-diacrylate (PEGDA). In another embodiment, the monomer is ethoxylated trimethylolpropane triacrylate (ETPTA). The molecular weight of the PEGDA and the ETPTA is any suitable molecular weight and can be selected by the person skilled in the art. In an embodiment, the average $M_n$ of the PEGDA is from about 200 to about 700. In another embodiment, the average $M_n$ of the PEGDA is about 200, about 575 or about 700. In a further embodiment, the average $M_n$ of the ETPTA is from about 428 to about 956. In another embodiment of the present application, the average $M_n$ of the ETPTA is about 428, about 693, about 912 or about 956.

In an embodiment, the molar ratio of the monomer to the anchor precursor is from about 10:1 to about 1:1. In another embodiment, the molar ratio of the monomer to the anchor precursor is about 10:1.

The photoreducer-photoinitiator is any suitable photoreducer-photoinitiator that is capable of photoreducing the cationic metal nanoparticle precursor and photoinitiating the polymerization of the photopolymerizable groups in the polymer microparticle precursor under the conditions used in the methods of the present application. In an embodiment, the photoreducer-photoinitiator is 2-hydroxy-2-methyl-1-phenyl-propan-1-one (Darocure™ 1173) or 2-hydroxy-4'-(2-hydroxyethoxy)-2-methylpropiophenone (Irgacure™ 2959). In another embodiment, the photoreducer-photoinitiator is 2-hydroxy-2-methyl-1-phenyl-propan-1-one. In a further embodiment, the photoreducer-photoinitiator is 2-hydroxy-4'-(2-hydroxyethoxy)-2-methylpropiophenone.

The wavelength of irradiation may depend, for example, on the selection of the photoreducer-photoinitiator and a suitable wavelength for a particular photoreducer-photoinitiator can be selected by a person skilled in the art. In some embodiments, the composition is irradiated at a wavelength of from about 100 nm to about 400 nm. In another embodiment, the composition is irradiated at a wavelength of from about 350 nm to about 380 nm or about 365 nm. The selection of a suitable source for the electromagnetic radiation for the irradiation can be made by a person skilled in the art.

In an embodiment, the composition is irradiated for a time of from about 1 second to about 15 seconds. In another embodiment, the composition is irradiated for a time of about 1, 2, 3, 4, 6, 9 or 15 seconds.

In an embodiment, the nanoparticles have an average diameter in the range of from about 10 nm to about 150 nm.

In some embodiments, the method further comprises functionalizing the surface of the polymer microparticle-metal nanoparticle with an analyte-binding biomolecule. As used herein, "functionalizing the surface of the polymer microparticle-metal nanoparticle with an analyte-binding biomolecule" refers to linking the polymer microparticle-metal nanoparticle with the analyte-binding biomolecule. In some embodiments, the linking is the result of a chemical bond between the polymer microparticle and the analyte-binding biomolecule. In an embodiment, the linking is via a covalent bond. In some embodiments, the functionalizing of the surface of the polymer microparticle-metal nanoparticle is carried out under conditions to directly link the polymer microparticle to the analyte-binding biomolecule. In other embodiments, the functionalizing of the surface of the polymer microparticle-metal nanoparticle is carried out under conditions so that a spacer is used to link the polymer microparticle with the analyte-binding biomolecule. In some embodiments, the analyte-binding biomolecule comprises a thiol, amine and/or carboxyl group and is linked to the surface by means of said group. The selection of suitable conditions can be readily selected by a person skilled in the art and will depend, for example, on the specific application and biomolecule of interest.

In an embodiment, the analyte-binding molecule comprises DNA (e.g. it is a DNA probe or an oligonucleotide aptamer) or protein (e.g. it is an antibody or a peptide aptamer). In another embodiment, the analyte-binding biomolecule is a DNA probe, an antibody or an aptamer.

In some embodiments, the composition further comprises a plurality of polymerase chain reaction (PCR) primers.

III. Composites

The present application also includes a polymer microparticle-metal nanoparticle composite. The present application also includes a surface-functionalized polymer microparticle-metal nanoparticle composite. In some embodiments, the composites are prepared by a method for preparing polymer microparticle-metal nanoparticle composites of the present application. It will be appreciated by a person skilled in the art that embodiments of the composites can be varied as described herein for the methods for preparing the polymer microparticle-metal nanoparticle composite of the present application.

The present application also includes a polymer microparticle-metal nanoparticle composite comprising a uniform distribution of metal nanoparticles embedded in a polymeric resin microparticle, the polymeric resin comprising a plurality of metal-anchoring groups, the metal anchoring groups anchored to the nanoparticles. The metal-anchoring groups can be any suitable metal-anchoring groups. In an embodiment, the metal anchoring groups are thiols, primary amines, silanes or combinations thereof. In another embodiment, the metal anchoring groups are thiols. In an embodiment, the metal-anchoring groups are derived from bi-functional thiols, bi-functional primary amines or bi-functional silanes (i.e. the metal-anchoring groups are introduced into the polymeric resin by a method comprising the use of an anchor precursor as that term is used herein that is a bi-functional thiol, bi-functional primary amine or bi-functional silane). In another embodiment, the metal anchoring groups are derived from dithiothreitol.

In an embodiment, the composite has an average diameter of from about 1 μm to less than 1 mm. In another embodiment, the composite has an average diameter of from about 1 μm to about 100 μm.

In an embodiment, the metal nanoparticles are gold nanoparticles, silver nanoparticles, copper nanoparticles or nanoparticles comprising a combination of two or more of gold, silver and copper. In another embodiment, the metal nanoparticles are gold nanoparticles. In a further embodiment, the metal nanoparticles are silver nanoparticles. It is an embodiment that the metal nanoparticles are copper nanoparticles. In another embodiment, the nanoparticles comprise a combination of two or more of gold, silver and copper.

In an embodiment, the metal nanoparticles are present in an amount of from about 0.1% wt to about 30% wt, based on the total weight of the composite.

In an embodiment, the nanoparticles have an average diameter in the range of from about 10 nm to about 150 nm.

The polymeric resin is any suitable polymeric resin. In an embodiment, the polymeric resin is an acrylate resin, an epoxy resin, a siloxane resin or combinations thereof. In an embodiment, the siloxane resin is derived from ring-opening polymerization of a monomer comprising a cyclic siloxane group. In another embodiment, the cyclic siloxane groups have a ring size of 6, 8 or 10. In a further embodiment, the cyclic siloxane group is a cyclic dimethylsiloxane group. In another embodiment, the siloxane resin is derived from an organoreactive siloxane. The term "organoreactive siloxane" as used herein refers to a siloxane resin precursor comprising photopolymerizable groups such as acrylate or epoxy groups). In another embodiment, the polymeric resin is an acrylate resin.

In an embodiment, the polymeric resin further comprises an oligomeric poly(ethylene glycol). In another embodiment, the polymeric resin is a poly(ethylene glycol)-diacrylate (PEGDA) resin or an ethoxylated trimethylolpropane triacrylate (ETPTA) resin. In a further embodiment, the polymeric resin is a PEGDA resin. It is an embodiment that the polymeric resin is an ETPTA resin. The molecular weight of the PEGDA and the ETPTA monomers comprised in the PEGDA and ETPTA resins, respectively is any suitable molecular weight and can be selected by the person skilled in the art. In an embodiment, the average $M_n$ of the PEGDA is from about 200 to about 700. In another embodiment, the average $M_n$ of the PEGDA is about 200, about 575 or about 700. In a further embodiment, the average $M_n$ of the ETPTA is from about 428 to about 956. In another embodiment of the present application, the average $M_n$ of the ETPTA is about 428, about 693, about 912 or about 956

In an embodiment, the molar ratio of the monomers comprised in the polymeric resin to the metal anchoring groups is from about 10:1 to about 1:1. In another embodiment, the molar ratio is about 10:1.

In some embodiments, the composite further comprises a plurality of analyte-binding biomolecules linked to the surface of the composite. In some embodiments, the linking is the result of a chemical bond between the polymer microparticle and the analyte-binding biomolecule. In an embodiment, the linking is via a covalent bond. In some embodiments, the polymer microparticle is directly linked to the analyte-binding biomolecule. In other embodiments, a spacer is used to link the polymer microparticle with the analyte-binding biomolecule. In some embodiments, the analyte-binding biomolecule comprises a thiol, amine and/or carboxyl group and is linked to the surface by means of said group. In an embodiment, the analyte-binding molecules comprise DNA (e.g. are DNA probes or oligonucleotide aptamers) or protein (e.g. are antibodies or peptide aptamers). In another embodiment of the present application, the analyte-binding molecules are DNA probes, antibodies or aptamers.

In an embodiment, the composite further comprises a plurality of PCR primers embedded in the polymer resin.

The present application also includes a drug delivery system comprising a suitable polymer microparticle-metal nanoparticle composite of the application. In some embodiments, the drug delivery system further comprises a drug. In some embodiments, the drug is an anti-cancer drug.

IV. Uses of Composites

The polymer microparticle-metal nanoparticle composites of the application are new therefore the present application includes all uses of the polymer microparticle-metal nanoparticle composites of the application, including, for example, use in therapeutic methods, diagnostic assays and as research tools.

In some embodiments, the polymer microparticle-metal nanoparticle composites of the application are for use in drug delivery, in microparticle-based colorimetric sensors, in micro-localized plasmonic bead heaters for PCR, surface plasmon resonance (SPR) or surface enhanced Raman spectroscopy (SERS) sensing elements, in antimicrobial beads or in other sensor devices.

In some embodiments, the drug delivery systems of the application comprise a drug. Accordingly, the present application also includes a method of treating a disease, disorder or condition treatable by a drug, the method comprising administering a drug delivery system of the application comprising the drug to a subject in need thereof. The present application also includes a use of a drug delivery system of the present application comprising a drug for treatment of a disease, disorder or condition treatable by the drug; a use of a drug delivery system of the present application comprising a drug for preparation of a medicament for treatment of a disease, disorder or condition treatable by the drug; and a drug delivery system of the present application comprising a drug for use to treat a disease, disorder or condition treatable by the drug. In some embodiments, the disease, disorder or condition is cancer and the drug is an anti-cancer drug. Accordingly, the present application also includes a method of treating cancer comprising administering a drug delivery system of the application comprising an anti-cancer drug to a subject in need thereof. The present application also includes a use of a drug delivery system of the present application comprising an anti-cancer drug for treatment of cancer; a use of a drug delivery system of the present application comprising an anti-cancer drug for preparation of a medicament for treatment of cancer; and a drug delivery system of the present application comprising an anti-cancer drug for use to treat cancer. It will be appreciated by a person skilled in the art that in such methods and uses, the drug delivery systems of the application are administered to the subject or for use such that the drug (e.g. the anti-cancer drug) is released from the composite and delivered to a target site. In some embodiments of the present application, the drug (e.g. the anti-cancer drug) is released by applying a means such as heat, a change in pH and/or irradiation with a suitable wavelength of light.

In some embodiments of the present application, the drug delivery systems of the application are used to deliver the metal nanoparticles for treatment of diseases, disorders or conditions treatable by the metal nanoparticles. Accordingly, the present application also includes a method of treating a disease, disorder or condition treatable by metal nanoparticles comprising administering a drug delivery system of the application to a subject in need thereof. The present application also includes a use of a drug delivery system of the present application for treatment of a disease, disorder or condition treatable by metal nanoparticles; a use of a drug delivery system of the present application for preparation of a medicament for treatment of a disease, disorder or condition treatable by metal nanoparticles; and a drug delivery system of the present application for use to treat a disease, disorder or condition treatable by metal nanoparticles. In an embodiment, the metal nanoparticles are gold nanoparticles. In some embodiments, the disease, disorder or condition is cancer and the metal nanoparticles are gold nanoparticles. Accordingly, the present application also includes a method of treating cancer comprising administering a drug delivery system of the application comprising gold nanoparticles to a subject in need thereof. The present application also includes a use of a drug delivery system of the present application comprising gold nanoparticles for treatment of cancer; a use of a drug delivery system of the present application comprising gold nanoparticles for preparation of a medicament for treatment of cancer; and a drug delivery system of the present application comprising gold nanoparticles for use to treat cancer. It will be appreciated by a person skilled in the art that in such methods and uses, the drug delivery systems of the application are administered to the subject or for use such that the metal nanoparticles are released from the composite and delivered to a target site.

Treatment comprises administering to a subject or use of an effective amount of the drug or the metal nanoparticles, optionally consisting of a single administration or use, or alternatively comprising a series of administrations or uses. For example, the administration or use is at least once a week. However, in another embodiment, the administration or use is from about one time per three weeks, or about one time per week to about once daily for a given treatment. In another embodiment, the administration or use is 2, 3, 4, 5 or 6 times daily. The length of the treatment period depends on a variety of factors, such as the severity of the disease, disorder or condition, the age of the subject, the activity of the drug, and/or a combination thereof. It will also be appreciated that the effective dosage of a drug or metal nanoparticles used for the treatment may increase or decrease over the course of a particular treatment regime. Changes in dosage may result and become apparent by standard diagnostic assays known in the art. In some instances, chronic administration or use is required. For example, the drug or metal nanoparticles are administered or used in an amount and for a duration sufficient to treat the subject.

The drug delivery systems of the application can be administered to a subject or used in a variety of forms depending on the selected route of administration or use, as will be understood by those skilled in the art. In an embodiment, the administration or use is subcutaneous, oral or transmucosal. A person skilled in the art would know how to prepare suitable formulations. It will be appreciated by a person skilled in the art that in the treatment methods and uses of the application, the drug delivery systems of the present application comprise pharmaceutically acceptable components.

Metal nanoparticles such as gold nanoparticles embedded in the polymer microparticles of the composites of the present disclosure can change color from red to purple, for example, in response to a refractive index change in the vicinity of the nanoparticle surface. For example, in embodiments of the composites of the present disclosure comprising an analyte-binding biomolecule (such as DNA, an antibody or an aptamer) linked to the surface, the color may change in proportion to analyte concentration when the analyte binds to the analyte-binding biomolecule. Accordingly, the present application also includes a colorimetric method for detecting the presence of an analyte in a liquid sample, the method comprising:

exposing a surface-functionalized polymer microparticle-metal nanoparticle composite of the present application which comprises an analyte binding biomolecule that binds the analyte, to the sample under conditions for the analyte-binding molecule to bind the analyte; and colorimetrically analyzing the sample after exposure to the composite to determine if the analyte was present in the sample.

The composite is exposed to the analyte by any suitable method, the selection of which can be made by a person skilled in the art. In an embodiment, the composite is contacted with the sample in the form of a dipstick. In an embodiment, the dipstick comprises a porous membrane and the composite is embedded in the porous membrane of the dipstick.

The present application also includes a use of a suitable microparticle-metal nanoparticle composite of the application as a plasmonic bead heater in a chamber for carrying out a polymerase chain reaction (PCR).

The present application also includes a use of a microparticle-metal nanoparticle composite of the application comprising a plurality of polymerase chain reaction (PCR) primers as a site for a PCR.

The following non-limiting examples are illustrative of the present application:

EXAMPLES

Example 1: Synthesis of Metallic Nanoparticle Loaded Polymer Microparticles

I. Materials and Methods

Monomer was prepared by mixing poly(ethylene glycol)-diacrylate (PEGDA) (MW 700 Da) with photoinitiator 2-hydroxy-2-methyl-1-phenyl-propan-1-one (Darocure 1173) at a concentration of 1% or as specified, followed by addition of gold chloride at a concentration of 100 mg/ml or as specified (0.1% wt to 30% wt). Alternatively, the monomer contained poly(ethylene glycol)-diacrylate (PEGDA) (MW 700 Da) reacted with 200 mg/ml dithiothreitol, DTT (aqueous solution) and mixed with photoinitiator 2-hydroxy-2-methyl-1-phenyl-propan-1-one (Darocure 1173) at a concentration of 1% or as specified, followed by addition of gold chloride at a concentration of 100 mg/ml or as specified (0.1% wt to 30% wt). In further experiments, the monomer was prepared by mixing ethoxylated trimethylolpropane triacrylate (ETPTA) with photoinitiator 2-hydroxy-2-methyl-1-phenyl-propan-1-one (Darocure 1173) at a concentration of 1% or as specified, followed by addition of gold chloride at a concentration of 100 mg/ml or as specified (0.1% wt to 30% wt). PEGDA with average $M_n$ from 200 g/mol to 700 g/mol was used. ETPTA with a MW of 428 g/mol (SR-454) and 693 g/mol (SR-502) from Sartomer was used.

The microparticle composite was prepared by co-flowing the monomer as inner phase with an immiscible outer phase (e.g. silicone, mineral or fluorocarbon oil) through a microfluidic junction of the droplet generator device in order to obtain monomer-in-oil emulsion. The generated monomer droplets were either exposed as they are being generated adjacent to the microfluidic junction or collected in the collection channel downstream and UV exposed. The exposure was performed either using a 365 nm high intensity UV point source (14 000 mW/cm$^2$), or a 200 Watt Mercury lamp with exposure time in the range of 1 sec to 15 sec.

Figure 2:
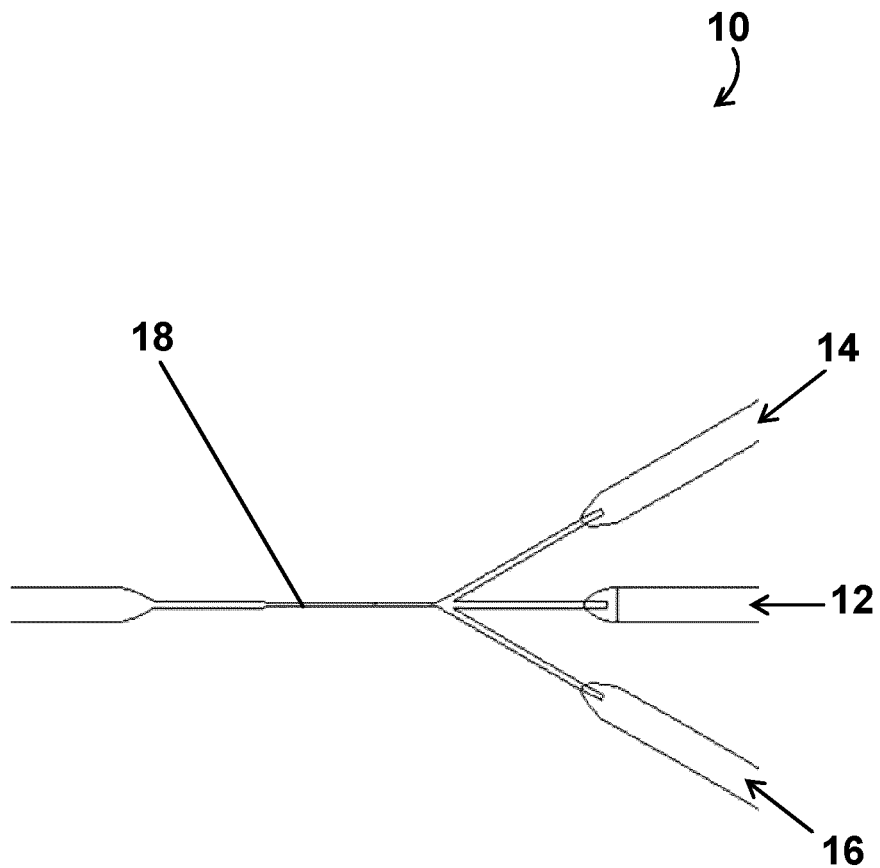
FIG. 2 is a schematic of a flow-focusing junction in a droplet microfluidics device according to an embodiment of the present application.
Figure 3:
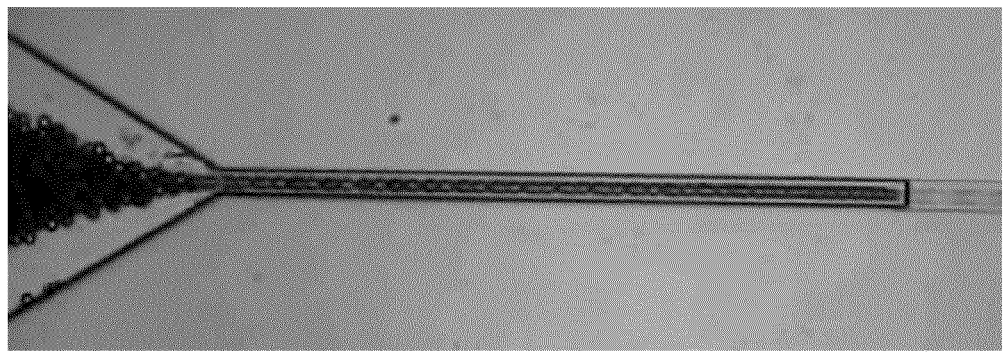
FIG. 3 is a microscope image showing droplet generation using a droplet microfluidics device with a flow-focusing junction according to an embodiment of the present application.

An example of the microfluidics device used is shown in FIG. 1. The microfluidics device is a standard device that can be used to generate droplets of various liquids, including monomers which can be polymerized. The microfluidics device includes a flow-focusing junction (denoted with *) that is used to generate microdroplets in the microfluidic channels. A schematic of an exemplary flow-focusing junction 10 is shown in FIG. 2. Referring to FIG. 2, by flowing the monomer solution as the dispersed phase 12 and an oil solution as the continuous phase (14, 16) a monomer-in-oil emulsion was obtained in the microchannel after the junction 18. By changing the flow velocity of the continuous and dispersed phases and the size of the junction, various droplet sizes can be obtained using such a microfluidics device (1 to 1000 µm). An example of the resulting monomer droplets generated is shown in FIG. 3.

Figure 4:
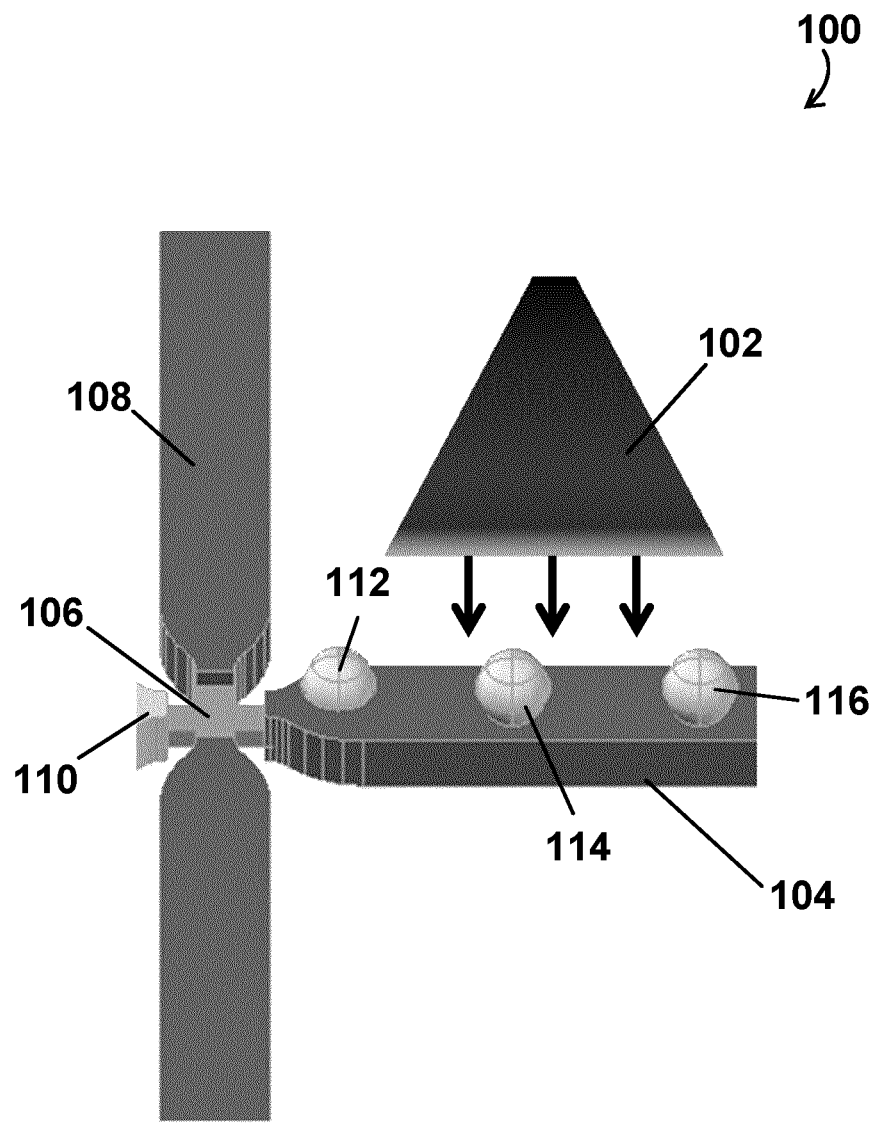
FIG. 4 is a schematic showing ultra-violet (UV) irradiation of droplets above a microfluidic channel in a droplet microfluidics device with a flow-focusing junction according to an embodiment of the present application.

Following the droplet generation, a UV point source was used to expose the droplet and polymerize the monomers to form a microparticle while simultaneously reducing the metal precursor into metallic nanoparticles. In the present studies, as shown in the schematic of an exemplary method 100 in FIG. 4, a UV point source 102 was placed above the microfluidic channel 104 following the droplet generation junction 106. Also shown in FIG. 4 are microchannels wherein the oil 108 and monomer solution 110 flow into junction 106 as well as the droplets prior to irradiation 112, being irradiated 114 and resulting polymer microparticle-metal nanoparticle composite 116. Alternatively, monomer droplets could be collected and exposed in a batch format using a UV lamp.

II. Results and Discussion

A method to obtain metal nanoparticle-polymer microparticle composites with well controlled metallic nanoparticle distribution throughout the polymer network and high nanoparticle content was investigated. The method used in-situ simultaneous reduction-polymerization of monomer droplets generated using microfluidics. UV generated radicals initiated the polyaddition reaction of the acrylic resin, and simultaneously reduced the Au$^{3+}$ in HAuCl$_4$ to Au$^0$, thus forming gold nanoparticles in situ during the polymer network formation.

Two monomers were used, poly(ethylene glycol)-diacrylate (PEGDA) and ethoxylated trimethylolpropane triacrylate (ETPTA), both of which undergo polymerization in the presence of a photoinitiator such as 2-hydroxy-2-methyl-1-phenyl-propan-1-one (Darocure™ 1173) or 2-hydroxy-4'-(2-hydroxyethoxy)-2-methylpropiophenone (Irgacure™ 2959). In some experiments, the monomer was first reacted with dithiothreitol (DTT) in aqueous solution. Subsequently, the resulting resin (monomer precursor composite) was used to fabricate the metal nanoparticle-polymer microparticle composites via UV polymerization of monomer droplets generated using droplet microfluidic technology. PEGDA or ETPTA reacted with DTT creates a polymer network with reactive thiol groups that can then be used to link gold (or silver) nanoparticles as they are created in the film, preventing their migration and subsequent agglomeration, resulting in monodisperse, uniformly distributed metal-polymer composites. In other words, when the bi-functional cross-linker dithiothreitol was reacted with the acrylic resin monomer prior to irradiation, the approach allowed one arm of the bi-functional cross-linker to become embedded in the polymer network, while the second arm remained free to be linked to the nanoparticles as they were generated in the film.

Figure 5:
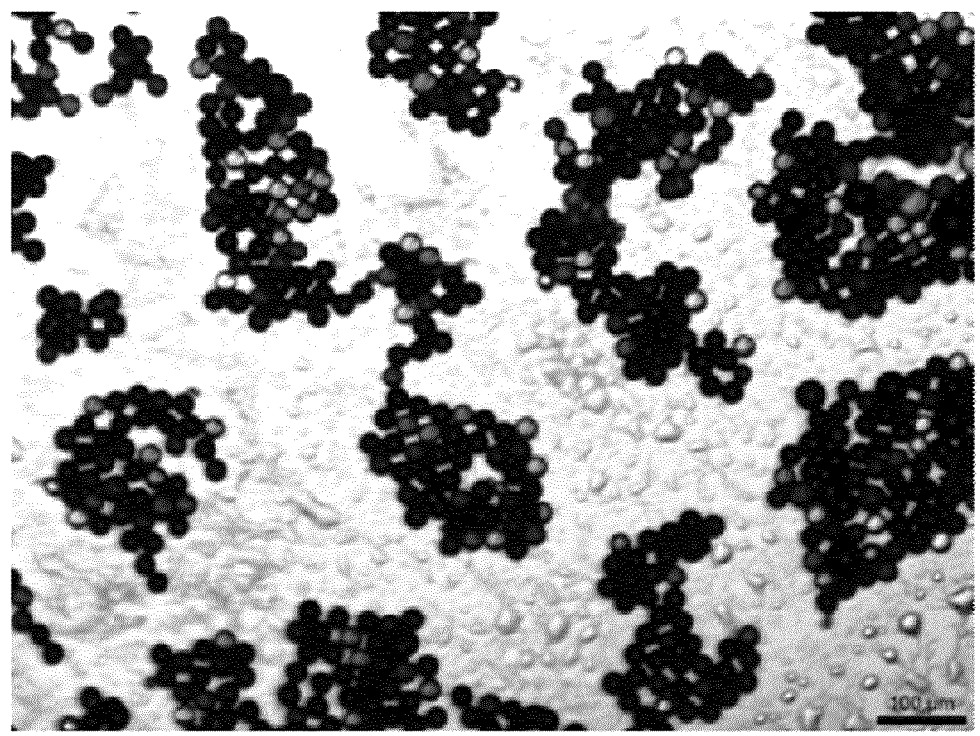
FIG. 5 is a microscope image of polymer microparticle-metal nanoparticle composites according to an embodiment of the present application wherein the monomer is poly(ethylene glycol)-diacrylate (PEGDA) and the metal nanoparticles are gold nanoparticles. Scale bar shows 100 µm.
Figure 6:
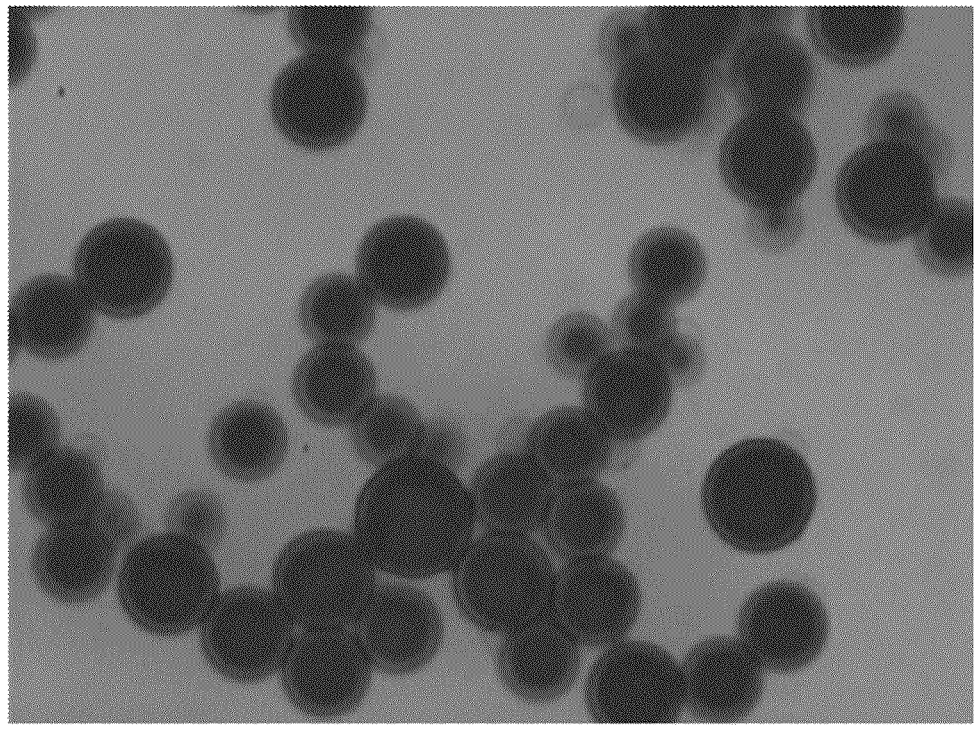
FIG. 6 is a microscope image of polymer microparticle-metal nanoparticle composites according to an embodiment of the present application wherein the monomer is ethoxylated trimethylolpropane triacrylate (ETPTA) and the metal nanoparticles are gold nanoparticles.
Figure 7:
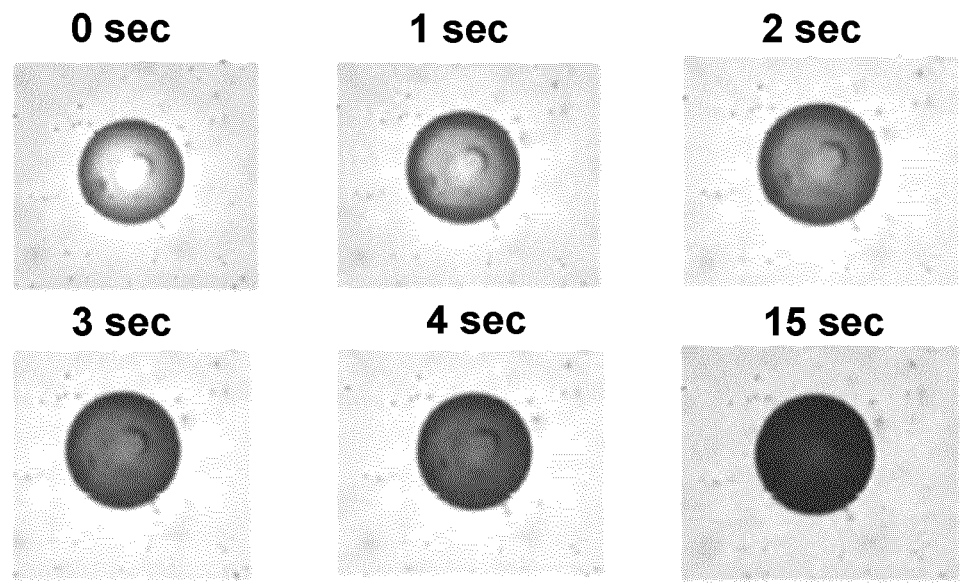
FIG. 7 shows real-time microscope images of a microparticle after 0 seconds (top left), 1 second (top center), 2 seconds (top right), 3 seconds (bottom left), 4 seconds (bottom center) and 15 seconds (bottom right) of irradiation according to embodiments of the present application.
Figure 8:
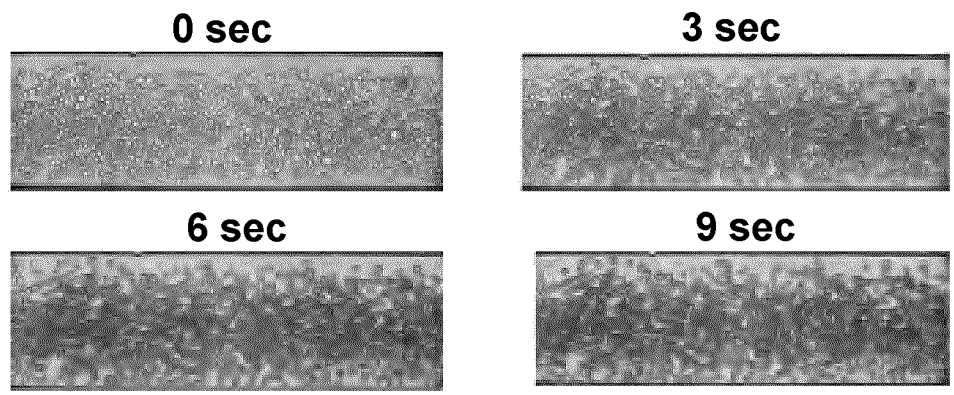
FIG. 8 shows real-time microscope images of microparticles after 0 seconds (top left), 3 seconds (top right), 6 seconds (bottom left) and 9 seconds (bottom right) of irradiation according to embodiments of the present application.

The resulting microparticles may be highly monodispersed and therefore may, for example, be suitable for industrial applications. Microscope images showing examples of polymer microparticle-metal nanoparticle composites wherein the monomer was PEGDA and ETPTA are shown in FIGS. 5 and 6, respectively. The fabricated polymer microparticle-metal nanoparticle composites exhibited different sizes of nanoparticles, as shown by different microparticle colors, which depended on the precursor concentration and exposure dose. Time-lapse images of microparticle exposure using a UV point source are shown in FIGS. 7 and 8, illustrating this dependence on the exposure dose. A higher exposure dose resulted in larger nanoparticle size (i.e. a darker microparticle, color shifted from yellow to pink, blue, deep red and purple). The nanoparticle size measured was in the range of 10 to 150 nm.

Figure 9:
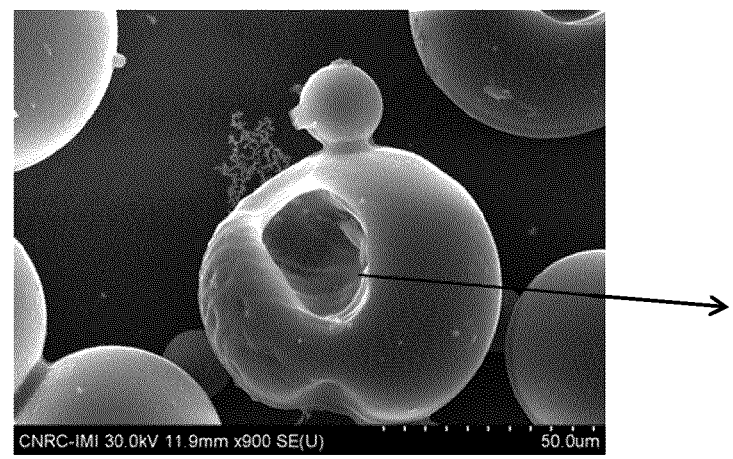
FIG. 9 shows scanning electron micrograph (SEM) images showing uniform nanoparticle distribution within a polymer microparticle-metal nanoparticle composite according to an embodiment of the present application. Middle and bottom images are successive magnifications of the top image as indicated by arrows. Scale bars show from top to bottom: 50.0, 10.0 and 3.0 µm. Inset in bottom image is a further magnification (scale bar shows 500 nm).
Figure 9:
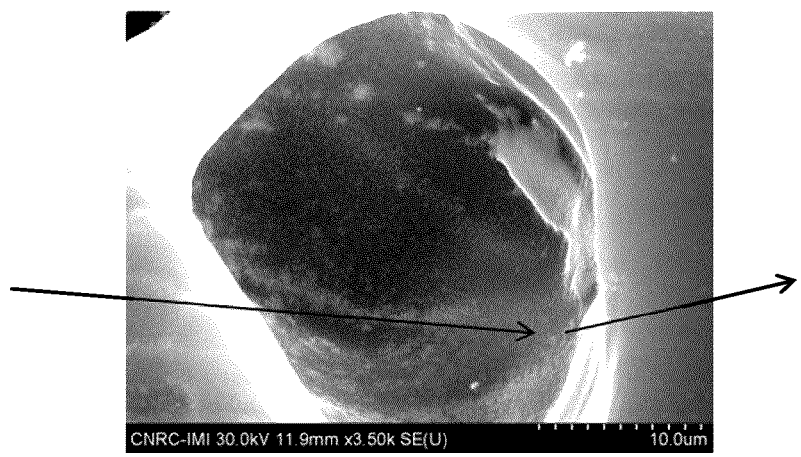
Figure 9:
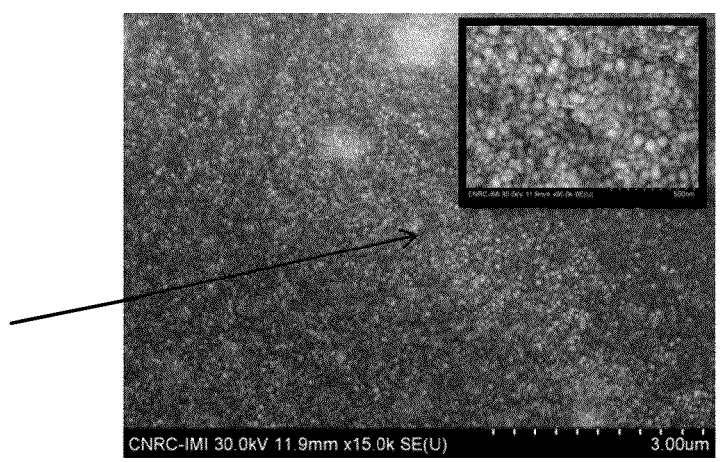
Figure 10:
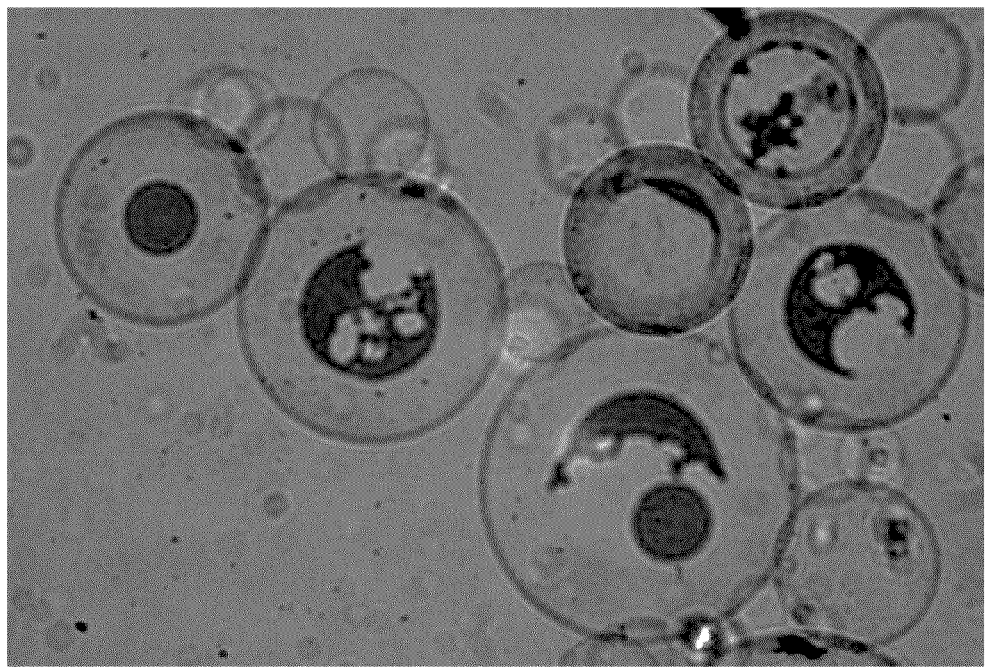
FIG. 10 is a microscope image showing gold nanoparticle concentration and agglomeration in the center of the polymer microparticles according to another embodiment of the present application.

Following exposure, depending on the microparticle composition (monomer with or without bi-functional cross-linker), the resulting nanoparticles were evenly distributed within the microparticles or agglomerated at specific microparticle regions. FIG. 9 shows a uniform distribution of gold nanoparticles within the polymeric microparticle, when the bi-functional cross-linker was used, while FIG. 10 shows gold nanoparticle concentration in the center of the fabricated microparticles when the bi-functional cross-linker was not used.

Commercial applications of such polymer microparticle-metal nanoparticle composites may include, for example, drug delivery, microparticle-based colorimetric sensors, micro-localized plasmonic bead heaters for PCR, surface plasmon resonance (SPR) or surface enhanced Raman spectroscopy (SERS) sensing elements, antimicrobial beads or other sensor devices.

Figure 11:
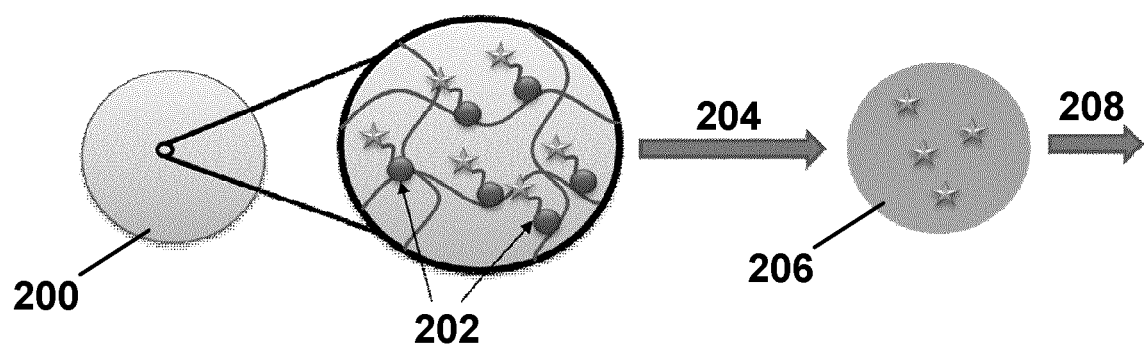
FIG. 11 is a schematic showing a use of a polymer microparticle-metal nanoparticle composite according to an embodiment of the present application for delivering an anti-cancer drug to a target cancer cell.

(a) Drug Delivery:

Hydrogels as drug delivery systems may be advantageous, for example, due to their effectiveness and biocompatibility. The gels are able to swell in aqueous solutions and can also undergo changes in shape or volume in response to physical or biological conditions such as temperature, pH, ionic concentration, or specific antigens. The use of gold nanoparticle-loaded microparticles (e.g. PEGDA microparticles) fabricated using microfluidic microemulsions according to the present example may, for example, enable facile actuation by visible light and/or microwave radiation or temperature. The gels may also be loaded with fluorescent or magnetic nanoparticles for advantageous delivery and/or detection. Such fluorescent or magnetic nanoparticles are dispersed in the composite precursor composition as nanoparticles. Any suitable fluorescent or magnetic nanoparticles could be used and can be selected by a person skilled in the art. For example, silica shell iron-oxide core nanoparticles are used. Thus the fabricated composites may, for example, have potential applications in microfluidic switches or microactuators, photosensors and/or nanomedicinal applications in controlled drug delivery and release. The core of the polymer gel microparticle embedded with gold nanoparticles may, for example, hold a liquid or a molecule that can be released over a range of temperatures and radiation wavelengths. Alternatively, gold nanoparticles may be released from the hydrogel and may inhibit proliferation of carcinoma cells, which may be used for controlled and targeted drug delivery. An example of a composite hydrogel 200 which includes gold nanoparticles 202 and an anti-cancer drug (*) is shown in FIG. 11. Referring to FIG. 11, upon subjecting the composite 200 to a means 204 for releasing the drug such as heat, a change in pH and/or irradiation with a suitable wavelength of light, the drug is released such that it may be delivered to a target cancer cell 206, destroying it 208.

Figure 12:
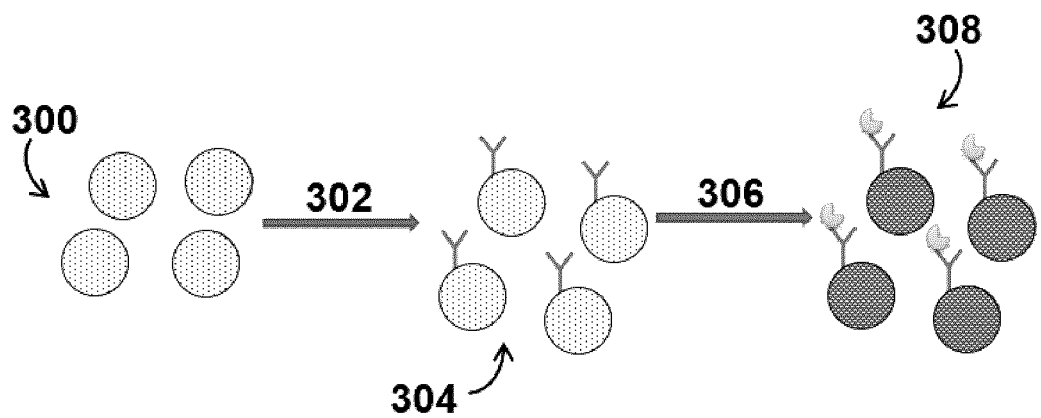
FIG. 12 is a schematic showing a use of a polymer microparticle-metal nanoparticle composite according to an embodiment of the present application as a colorimetric sensor for detecting a target analyte.

(b) Polymer Microparticle-Gold Nanoparticle Composite-Based Colorimetric Sensor (or SPR/SERS Sensor):

Gold nanoparticles embedded in the polymer microparticles can change color from red to purple in response to a refractive index change in the vicinity of the nanoparticle surface. For example, an analyte-binding biomolecule such as DNA, an antibody or an aptamer can be easily attached to the composite microparticles and when the analyte binds to the analyte-binding biomolecule, the color changes in proportion to analyte concentration. An advantage of this approach in comparison to traditional batch fabrication of gold nanoparticles may be a significantly reduced production time. Colorimetric-based sensing using this approach may, for example, be implemented in the format of solution-based sensing with the polymer microparticle-metal nanoparticle composites suspended in a solution of interest. FIG. 12 shows a schematic of an exemplary method wherein isolated PEGDA microparticle-gold nanoparticle composites 300 (red in color) are functionalized 302 with an analyte-binding biomolecule to provide PEGDA microparticle-gold nanoparticle composites functionalized with an analyte-binding biomolecule such as an antibody 304. After a bio-recognition event 306 whereby the analyte binds with the analyte-binding biomolecule 308, the local refractive index in the vicinity of the gold nanoparticles is shifted towards the color purple.

Figure 13:
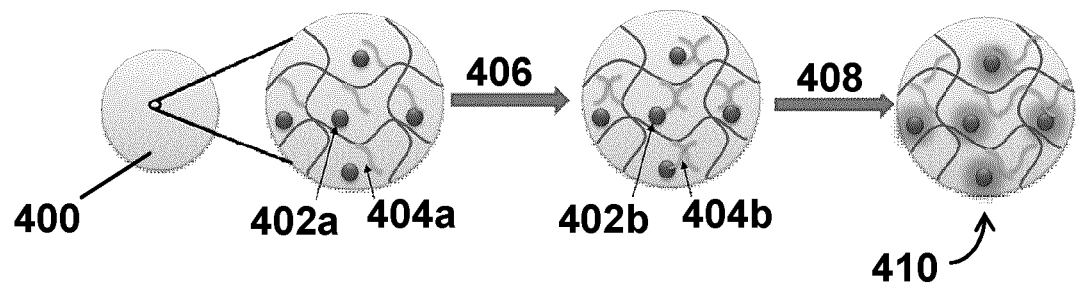
FIG. 13 is a schematic showing a use of a polymer microparticle-metal nanoparticle composite according to an embodiment of the present application as a plasmonic bead heater for polymerase chain reaction (PCR).

(c) Microlocalized Plasmonic Bead Heaters for PCR:

polymer (e.g. PEGDA) microparticles comprising gold nanoparticles generated on the fly via UV polymerization of polymer (e.g. PEGDA) microbeads may, also, for example, serve as micro-localized heaters for standard PCR chambers and applications. Alternatively, polymer (e.g. PEGDA) microparticle-gold nanoparticle composite hydrogel beads may also potentially serve as localized PCR sites. For example, droplets containing the PEGDA and Au precursors mixed with PCR primers are solidified using irradiation according to a method disclosed herein to obtain a composite comprising the PCR primer. When suspended in a solution containing target DNA, the DNA may then, for example, pass through the porous composite beads and amplification may be carried out by changing the local temperature, for example, through plasmonic heating of the gold nanoparticles embedded in the composite beads via light irradiation. This may be advantageous for single-cell detection or very small volume PCR (digital PCR). An example of a composite hydrogel 400 which includes gold nanoparticles (402a, 402b) and a PCR primer (404a, 404b) is shown in FIG. 13. Referring to FIG. 13, the composite 400 is mixed 406 with a sample comprising target DNA then irradiated 408 with light to change the local temperature 410.

While the present application has been described with reference to what are presently considered to be the preferred examples, it is to be understood that the application is not limited to the disclosed examples. To the contrary, the present application is intended to cover various modifications and equivalent arrangements included within the spirit and scope of the appended claims.

All publications, patents and patent applications are herein incorporated by reference in their entirety to the same extent as if each individual publication, patent or patent application was specifically and individually indicated to be incorporated by reference in its entirety. Where a term in the present application is found to be defined differently in a document incorporated herein by reference, the definition provided herein is to serve as the definition for the term.

FULL CITATIONS FOR DOCUMENTS REFERRED TO IN THE DESCRIPTION

[1] Eustis, Susie, and Mostafa A. El-Sayed. "Why gold nanoparticles are more precious than pretty gold: noble metal surface plasmon resonance and its enhancement of the radiative and nonradiative properties of nanocrystals of different shapes." *Chemical Society Reviews* 35.3 (2006): 209-217.

[2] Trojanowska, Anna, et al. "Plasmonic-polymer hybrid hollow microbeads for surface-enhanced Raman scattering (SERS) ultradetection." *Journal of Colloid and Interface Science* 460 (2015): 128-134.

[3] Farah, Abdiaziz A., Ramon A. Alvarez-Puebla, and Hicham Fenniri. "Chemically stable silver nanoparticle-crosslinked polymer microspheres." *Journal of Colloid and Interface Science* 319.2 (2008): 572-576.

[4] Yagci, Yusuf, Marco Sangermano, and Giancarlo Rizza. "In situ synthesis of gold-cross-linked poly (ethylene glycol) nanocomposites by photoinduced electron transfer and free radical polymerization processes." *Chemical Communications* 24 (2008): 2771-2773.

[5] Von Werne, Timothy, and Timothy E. Patten. "Preparation of structurally well-defined polymer-nanoparticle hybrids with controlled/living radical polymerizations." *Journal of the American Chemical Society* 121.32 (1999): 7409-7410.

[6] Wilhelm, T. S. "Microdroplet fabrication of silver-agarose nanocomposite beads for SERS optical accumulation." *Soft Matter* 7.4 (2011): 1321-1325.

[7] Abalde-Cela, Sara, et al. "Loading of exponentially grown LBL films with silver nanoparticles and their application to generalized SERS detection." *Angewandte Chemie* 121.29 (2009): 5430-5433.

[8] Yagci, Yusuf, Marco Sangermano, and Giancarlo Rizza. "In situ synthesis of gold cross-linked poly (ethylene glycol) nanocomposites by photoinduced electron transfer and free radical polymerization processes." *Chemical Communications* 24 (2008): 2771-2773.

[9] (a) Teh, Shia-Yen, et al. "Droplet microfluidics." *Lab on a Chip* 8.2 (2008): 198-220; (b) i Solvas, Xavier Casadevall. "Droplet microfluidics: recent developments and future applications." *Chemical Communications* 47.7 (2011): 1936-1942; (c) Shum, Ho Cheung, et al. "Droplet Microfluidics for Fabrication of Non-Spherical Particles." *Macromolecular rapid communications* 31.2 (2010): 108-118.

[10] Xu, Shengqing, et al. "Generation of monodisperse particles by using microfluidics: control over size, shape, and composition." *Angewandte Chemie* 117.5 (2005): 734-738.

[11] Dendukuri, D. et al., "Continuous-flow lithography for high-throughput microparticle synthesis" *Nat. Mater.* 2006, 5, 365-369.

The invention claimed is:

1. A method for preparing a polymer microparticle-metal nanoparticle composite, the method comprising:
 introducing into a microfluidic device, a composition comprising:
 a cationic metal nanoparticle precursor;
 a polymer microparticle precursor that comprises a plurality of photopolymerizable groups and a plurality of metal-anchoring groups; and
 a photoreducer-photoinitiator; and
 irradiating the composition under conditions to simultaneously reduce the cationic metal and polymerize the photopolymerizable groups to obtain the polymer microparticle-metal nanoparticle composite,
 wherein the polymer microparticle-metal nanoparticle composite comprises a uniform distribution of metal nanoparticles embedded in a polymeric resin microparticle, the polymeric resin comprising the plurality of metal-anchoring groups, wherein the metal-anchoring groups are derived from bi-functional thiols, and wherein the metal anchoring groups are anchored to the nanoparticles.

2. The method of claim 1, wherein the cationic metal nanoparticle pre-cursor is a cationic gold nanoparticle precursor, a cationic silver nanoparticle precursor, a cationic copper nanoparticle precursor or combinations thereof.

3. The method of claim 1, wherein the polymer microparticle precursor is obtained from a method comprising:
 reacting a monomer comprising two or more photopolymerizable groups with an anchor precursor comprising at least one metal-anchoring group and at least one group that will react with the photopolymerizable group.

4. The method of claim 3, wherein the monomer further comprises an oligomeric poly(ethylene glycol).

5. A polymer microparticle-metal nanoparticle composite comprising a uniform distribution of metal nanoparticles embedded in a polymeric resin microparticle, the polymeric resin comprising a plurality of metal-anchoring groups, wherein the metal-anchoring groups are derived from bi-functional thiols, and wherein the metal anchoring groups are anchored to the nanoparticles.

6. The composite of claim 5, wherein the metal nanoparticles are gold nanoparticles, silver nanoparticles, copper nanoparticles or nanoparticles comprising a combination of two or more of gold, silver and copper.

7. The composite of claim 5, wherein the polymeric resin is an acrylate resin.

8. The composite of claim 5, wherein the polymeric resin further comprises an oligomeric poly(ethylene glycol).

9. The composite of claim 5, further comprising a plurality of analyte-binding biomolecules linked to the surface of the composite.

10. The composite of claim 5, wherein the composite has an average diameter of from about 1 µm to about 100 µm.

11. The composite of claim 6, wherein the metal nanoparticles are gold nanoparticles.

12. The composite claim 5, wherein the metal nanoparticles are present in an amount of from about 0.1% wt to about 30% wt, based on the total weight of the composite.

13. The composite of claim 5, wherein the metal anchoring groups are derived from dithiothreitol.

14. The composite of claim 5, wherein the polymeric resin is a poly(ethylene glycol)-diacrylate (PEGDA) resin or an ethoxylated trimethylolpropane triacrylate (ETPTA) resin.

15. The composite of claim 14, wherein the polymeric resin is a PEGDA resin.

16. The composite of claim 9, wherein the analyte-binding molecules are DNA probes, antibodies or aptamers.

17. The composite of claim 5, further comprising a plurality of polymerase chain reaction primers embedded in the polymer resin.

* * * * *